(12) United States Patent
Heide et al.

(10) Patent No.: US 12,048,790 B2
(45) Date of Patent: Jul. 30, 2024

(54) THERAPY CONTROL BY COMPREHENSIVE FEEDBACK

(71) Applicants: Fresenius Medical Care Deutschland GmbH, Bad Homburg (DE); Fresenius Medical Care Holdings, Inc., Waltham, MA (US)

(72) Inventors: Alexander Heide, Eppstein (DE); Karsten Fischer, Schweinfurt (DE); Stephen A. Merchant, Oklahoma City, OK (US)

(73) Assignees: Fresenius Medical Care Deutschland GmbH, Bad Homburg (DE); Medical Care Holdings, Inc., Waltham, MA (US)

( * ) Notice: Subject to any disclaimer, the term of this patent is extended or adjusted under 35 U.S.C. 154(b) by 54 days.

(21) Appl. No.: 17/074,184

(22) Filed: Oct. 19, 2020

(65) Prior Publication Data
US 2021/0030939 A1 Feb. 4, 2021

Related U.S. Application Data

(62) Division of application No. 15/636,713, filed on Jun. 29, 2017, now Pat. No. 10,842,924.

(51) Int. Cl.
*A61M 1/16* (2006.01)
*A61B 5/00* (2006.01)
(Continued)

(52) U.S. Cl.
CPC ......... *A61M 1/1601* (2014.02); *A61B 5/0015* (2013.01); *A61B 5/11* (2013.01);
(Continued)

(58) Field of Classification Search
CPC . A61B 2560/0242; A61B 5/0015; A61B 5/11; A61B 5/4809; A61B 5/4836;
(Continued)

(56) References Cited

U.S. PATENT DOCUMENTS 5,910,252 A   6/1999 Truitt et al.
6,427,088 B1  7/2002 Bowman
(Continued)

FOREIGN PATENT DOCUMENTS

CN   102198301   9/2011
CN   203181054   9/2013
(Continued)

OTHER PUBLICATIONS

International Search Report and Written Opinion in International Application No. PCT/EP2018/067194, dated Oct. 11, 2018, 14 pages.

*Primary Examiner* — Dirk R Bass
(74) *Attorney, Agent, or Firm* — Fish & Richardson P.C.

(57) ABSTRACT

The application refers to a medical treatment device a medical treatment system and a method for operating the medical treatment device and medical treatment system for treatment of a patient, comprising a sensor interface for receiving sensor data from a plurality of different external and internal peripheral sensors, a controller for processing the received sensor data in order to calculate control data and for providing the calculated control data for controlling medical treatment-related devices or for controlling a configuration of medical treatment-related apparatuses and an output interface for providing the control data.

20 Claims, 4 Drawing Sheets

(51) Int. Cl.
  *A61B 5/11* (2006.01)
  *A61M 1/28* (2006.01)
  *A61M 21/02* (2006.01)
  *A61M 39/08* (2006.01)
  *A61M 60/109* (2021.01)
  *A61M 60/232* (2021.01)
  *A61M 60/37* (2021.01)
  *A61M 60/531* (2021.01)
  *A61M 60/554* (2021.01)
  *G16H 40/63* (2018.01)
  *G16H 40/67* (2018.01)
  *A61M 21/00* (2006.01)

(52) U.S. Cl.
  CPC .......... *A61B 5/4809* (2013.01); *A61B 5/4836* (2013.01); *A61B 5/4848* (2013.01); *A61B 5/6801* (2013.01); *A61M 1/28* (2013.01); *A61M 21/02* (2013.01); *A61M 39/08* (2013.01); *A61M 60/109* (2021.01); *A61M 60/232* (2021.01); *A61M 60/37* (2021.01); *A61M 60/531* (2021.01); *A61M 60/554* (2021.01); *G16H 40/63* (2018.01); *G16H 40/67* (2018.01); *A61B 2560/0242* (2013.01); *A61M 2021/0027* (2013.01); *A61M 2021/0044* (2013.01); *A61M 2021/0083* (2013.01); *A61M 2205/18* (2013.01); *A61M 2205/3368* (2013.01); *A61M 2205/3553* (2013.01); *A61M 2205/3569* (2013.01); *A61M 2205/3584* (2013.01); *A61M 2205/50* (2013.01); *A61M 2205/502* (2013.01); *A61M 2205/52* (2013.01); *A61M 2205/587* (2013.01); *A61M 2230/06* (2013.01); *A61M 2230/30* (2013.01); *A61M 2230/50* (2013.01)

(58) Field of Classification Search
  CPC .. A61B 5/4848; A61B 5/6801; A61M 1/1005; A61M 1/101; A61M 1/1086; A61M 1/1601; A61M 1/28; A61M 2021/0083; A61M 21/02; A61M 2205/18; A61M 2205/3368; A61M 2205/3553; A61M 2205/3569; A61M 2205/3584; A61M 2205/50; A61M 2021/0027; A61M 2021/0044; A61M 2205/502; A61M 39/08; A61M 60/205; A61M 60/50; A61M 60/562; G16H 40/63; G16H 40/67
  See application file for complete search history.

(56) References Cited

U.S. PATENT DOCUMENTS

| | | | |
|---|---|---|---|
| 6,562,001 | B2 | 5/2003 | Lebel et al. |
| 6,564,105 | B2 | 5/2003 | Starkweather et al. |
| 6,571,128 | B2 | 5/2003 | Lebel et al. |
| 6,577,899 | B2 | 6/2003 | Lebel et al. |
| 6,585,644 | B2 | 7/2003 | Lebel et al. |
| 6,635,014 | B2 | 10/2003 | Starkweather et al. |
| 6,648,821 | B2 | 11/2003 | Lebel et al. |
| 6,659,948 | B2 | 12/2003 | Lebel et al. |
| 6,668,196 | B1 | 12/2003 | Villegas et al. |
| 6,673,314 | B1 | 1/2004 | Burbank et al. |
| 6,687,546 | B2 | 2/2004 | Lebel et al. |
| 6,694,191 | B2 | 2/2004 | Starkweather et al. |
| 6,695,806 | B2 | 2/2004 | Gelfand et al. |
| 6,733,446 | B2 | 5/2004 | Lebel et al. |
| 6,740,075 | B2 | 5/2004 | Lebel et al. |
| 6,758,810 | B2 | 7/2004 | Lebel et al. |
| 6,810,290 | B2 | 10/2004 | Lebel et al. |
| 7,237,121 | B2 | 6/2007 | Cammack et al. |
| 7,857,976 | B2 | 12/2010 | Bissler et al. |
| 7,875,168 | B2 | 1/2011 | Fressinet et al. |
| 7,922,899 | B2 | 4/2011 | Vasta et al. |
| 7,938,796 | B2 | 5/2011 | Moubayed et al. |
| 8,025,634 | B1 | 9/2011 | Moubayed et al. |
| 8,425,767 | B2 | 4/2013 | Fava et al. |
| 8,775,196 | B2 | 7/2014 | Simpson et al. |
| 9,002,655 | B2 | 4/2015 | Bene |
| 9,132,217 | B2 | 9/2015 | Soykan et al. |
| 9,138,526 | B2 | 9/2015 | Ware et al. |
| 9,144,639 | B2 | 9/2015 | Vantard et al. |
| 9,199,026 | B2 | 12/2015 | Greenberg et al. |
| 9,199,027 | B2 | 12/2015 | Fontanazzi et al. |
| 9,289,545 | B2 | 3/2016 | Olde et al. |
| 9,561,316 | B2 | 2/2017 | Gerber et al. |
| 9,597,440 | B2 | 3/2017 | Gerber et al. |
| 9,642,960 | B2 | 5/2017 | Gerber et al. |
| 2006/0241543 | A1 | 10/2006 | Gura |
| 2007/0276270 | A1 | 11/2007 | Tran |
| 2013/0193041 | A1 | 8/2013 | Rohde |
| 2014/0121845 | A1 | 5/2014 | Mueller |
| 2016/0228640 | A1* | 8/2016 | Pindado ............. A61N 1/37282 |

FOREIGN PATENT DOCUMENTS

| | | |
|---|---|---|
| CN | 104937597 | 9/2015 |
| WO | WO 2013/076481 | 5/2013 |

* cited by examiner

THERAPY CONTROL BY COMPREHENSIVE FEEDBACK

CROSS-REFERENCE TO RELATED APPLICATIONS

This application is a divisional application of and claims priority to U.S. application Ser. No. 15/636,713, filed on Jun. 29, 2017.

TECHNICAL FIELD

The present disclosure relates to an automatic control of a medical treatment device, a medical treatment device and a medical treatment system and in particular relates to an automatic control of home dialysis machines.

BACKGROUND

A medical treatment device, such as a dialysis machine, is a complex apparatus and the respective procedure for operating the apparatus necessitates know how and sophisticated medical treatment equipment. Usually, the patient is immobilized during operation, i.e., during periods of blood dialysis for separation of toxic accumulations.

The dialysis device may be used as a monolithic separate system or as part of a larger medical facility. The devices and systems can perform hemodialysis, hemofiltration, hemodiafiltration or peritoneal dialysis. The devices and systems include an electrodialyzer, chemical sorbents, electronic sensors, an electronic controller and a flow control apparatus.

During operation of typical dialysis machines performing hemodialysis, blood is passed through a dialysis chamber on one side of a dialysis membrane and a dialysate is passed on the other side of the dialysis membrane. In addition to diffusion of solutes across the dialysis membrane, a difference in pressure between the blood-side and the dialysate-side of the dialysis membrane drives the bulk movement of water from higher pressure to lower pressure. The pressure generated on a particular side of the dialysis membrane depends on several factors including flow rate, viscosity of the fluid, geometry of the dialyzer and physiological condition of the patient. The diffusion of impurities from the blood, across the dialysis membrane and into the dialysate is thermodynamically driven by the concentration gradient difference between the concentration of impurities in the blood and the concentration of those species in the dialysate.

As mentioned above, during dialysis treatment, the patient is usually immovably positioned at the dialysis machine and only has few options for distraction and therefore may perceive the treatment period as being inconvenient.

Home medical treatment may be particularly challenging because the patient is left on his or her own without support of clinic staff. Further, he or she needs to be motivated to use the medical treatment device reliably and regularly and in the dedicated, defined manner intended.

SUMMARY

The present application relates to a method for automatic control of a medical treatment device, a medical treatment device, a medical treatment system, a computer program and a data carrier.

Certain aspects relate to using an extensive but specific selection of sensor data for controlling the medical treatment device and for related devices and machines. "Related" in this respect refers to machines, products and electronic devices (medical and non-medical) which may be used during medical treatment, such as media devices, a lighting system, a phone system etc.

A first aspect relates a method for automatic control of a medical treatment device, such as a dialysis machine, in particular a home dialysis machine, a peritoneal dialyses machine. The control is based on sensor data from a plurality of sensors. The method comprises the steps:

Receiving sensor data from a plurality of (different) external or internal peripheral sensors. The sensors may be healthcare sensors (for example for receiving physiological data of the patient, like blood pressure, respiratory rate, electrical conductivity of the patient's skin) and non-healthcare sensors (e.g. position sensors). The sensors may be of different kind, like temperature sensor, a location sensor (e.g. GPS sensor).

Processing the received sensor data in order to aggregate the same and to calculate control data. The control data is adapted and may be used for control of the medical treatment process, including the medical treatment as such (e.g. dialysis) and related treatments (heat application, provision of music etc.).

Providing control data for controlling medical treatment-related devices (dialysis machine itself or connected devices) or for controlling a configuration of medical treatment-related apparatuses (disposables, such as a tube system).

This method has the advantage that peripheral devices which might be activated during medical treatment (radio, music player, telephone etc.) may be controlled in accordance with the operation of the medical treatment. For example, the control data may deactivate a wired telephone device, positioned apart from the medical device, because the patient may not reach the telephone during medical treatment. Only the patient's mobile device may be activated if the patient carries it with him or her. Another advantage is that the medical device and its assembly units (for example loudspeakers) are controlled such as to be adapted to the ambient conditions. If, for example, peripheral sensor data detects that the environment is very noisy, the loudspeakers of the medical treatment device may be controlled to output acoustical signals louder. Otherwise, if sensor data suggests a very silent environment, the volume of the acoustical output signals of the treatment device may be reduced, respectively. Another example may refer to the brightness of the displays of the treatment device which may be controlled in accordance with sensor signals extracted from an external lighting system and vice versa.

In a preferred embodiment, the sensor data comprises medical data and health related data of the patient, for instance, anamnestic data. The medical data and health related data may refer to actual and/or historical data of the patient. This aspect may help to improve the medical efficiency and may adapt the medical treatment more specifically to the patient.

In another preferred embodiment, the sensor data comprises non-healthcare data, like position data, temperature data, media data, acoustical data and/or insurance data of the patient. The ability to dynamically adapt to different situations may be an advantage of the method.

In another preferred embodiment, the sensor data comprises data selected of the group of consisting of: location data, physiological data, temperature data, scheduling data detectable in an electronic calendar, actual data, which are detected from wearables. The sensor data may relate to actual data and/or to historical data. The ability to dynamically adapt to different situations may be an advantage of the method.

In another preferred embodiment, the sensor data comprises:
Prior treatment data, which are detected prior to medical treatment,
Treatment data, which are detected during medical treatment and
Post treatment data, which are detected after medical treatment.

In another preferred embodiment, the sensor data comprises:
Location data, defining the actual position of the patient;
Movement pattern data, defining typical movements of the patient in connection with the medical treatment;
Environmental data, defining physical values for the medical treatment device;
Medical status data and/or health status data of the patient (comprising e.g.: blood pressure data, pulse, respiratory rate, electrical conductivity of the skin).

According to another preferred embodiment, the sensor data comprises physiological parameters (for instance pulse, blood pressure and/or respiratory rate . . . ) and wherein the control data comprises a blood pump control signal for controlling the blood pump.

According to another preferred embodiment, the sensor data comprises physiological parameters (pulse, blood pressure, respiratory rate etc.) and wherein the control data comprises a wake/sleep signal for supporting a wake state or a sleep state of the patient in accordance with the detected physiological parameters. This has the technical effect that the machine may help in initiating a sleep state of the patient, in case the sensor data suggests that the patient is usually falling asleep during medical treatment. Other contraindicated measures (playing music) are then automatically prevented.

According to another preferred embodiment, the threshold values are configured for all sensor data and wherein in case of non-compliance with at least one threshold, an alert signal is provided. This feature supports an early alarm in case of breach with health-related limitation parameters. According to a further aspect, these limitation parameters may be adapted dynamically, based on calculated control data.

According to another preferred embodiment, all sensor data and all control data are tracked and stored. Also, the aggregated data (sensor and control data) may be fed back to the system. A back propagation algorithm may be used for implementation. With this back propagation method the system may be implemented as a self-learning system. The system may be provided as neural network. The neural network may be trained with training data. The sensor data and control data may serve as training data. Reference data may also serve as training data.

The control data is a dataset with a set of control values for different control parameters for controlling different electronic devices. For example, the control dataset comprises first control data for controlling the DVD player, second control data for controlling the volume of the radio, third control data for controlling the external lighting system, forth control data for controlling internal brightness of the display(s), fifth control data for controlling heating temperatures and so forth. Thus, according to this preferred embodiment, the control data is multimodal and serves to control a set of different electronic systems and devices, which may be internal or external to the medical treatment device.

The control data is adapted and used to control the medical treatment device. The control data is provided to the medical treatment device via an appropriate interface. They may be provided from an external computer-based, electronic controller. The controller may also be integrated into the medical treatment device. In another preferred embodiment, the control data may be adapted and used to control not the medical treatment machine itself but related machines and means. The term "related machines" refers to apparatuses and electronic devices and machines which may be activated or used during the course of treatment, like inter alia radio, media device, headphones, heating devices, blind or shutter which are controllable electronically and/or other peripheral devices.

The control data may be forwarded directly to the related machine. The control data may be transferred according to a control protocol. The control protocol may be adapted to transfer a pre-processed control information data packet. The control information data packet may comprise meta data for more specifically controlling the respective related machine. The meta data may relate to authorization data, so that only in case an authorization for control of the related machine is given, the control information data packet will be sent to the related machine and otherwise the control access will be denied. This aspect enhances the security of the control method and helps to prevent unauthorized access to peripheral devices for which the user or other authorities want to delimit automatic control.

According to another preferred embodiment, the control data may only be transferred to the respective reception node (medical treatment apparatus itself or related machines etc.) if a confirmation signal is received. Typically, the user will get the option to confirm the control suggestion which has been generated automatically by the computing entity/program. For example, if the control signal refers to an increase in temperature, a respective information message ("temperature will be increased") may be provided on a user interface as well as a confirmation button or another means (for instance means for acoustic input of the confirmation signal), so that the user may confirm or reject the control suggestion. Thus, control by the generated control data is only triggered in case the control suggestion has been confirmed by the user. This improves security of the system.

According to another preferred embodiment, a control status is detected automatically. In case control data was sent to the medical treatment device or to the related machines or was output for the configuration of medical treatment related apparatuses, the status will be changed from "normal use" to "automatic control". This control status may be represented in a flag of a control status message. The control status message may be output on a user interface and/or may be forwarded via a network connection to a central server, for instance a server of a clinical institution which takes care for all medical treatments and stores respective data in a central database. This has the technical effect that the control status may be supervised and stored centrally.

In a preferred embodiment, the control data is processed to provide adapted limitation values for monitoring of the medical treatment process. For example, if it is detected that the patient is only using the medical treatment device in a certain time phase, for instance during night, the scheduling time limits for activating the medical treatment device may be adapted accordingly in order to prevent misuse of the device in unusual time intervals (in the example above, during the day). A breach of limitation values may be reported. In case a confirmation signal is received, activation may be triggered. However, in case the sensor data detects that the usage behavior of the patient changes over time and that the usage period changes (from night to daytime), the limitation values may be adapted accordingly (to prevent unusual usage during night time).

In a preferred embodiment, the term "related apparatuses" refers to apparatuses which are used during medical treatment, such as disposables. The disposables may for example and preferably comprise a tube system for a dialysis machine. In terms of costs and due to medical reasons it is, for example, important to adapt the tube length to the respective actual dialysis situation, which sometimes affords long tubes and sometimes the tubes may be shorter. Generally, the length of the tubes should be as short as possible in order to keep the amount of blood in the extracorporeal blood circulation as small as possible, which in turn reduces health risks. Further short tubes help to reduce (material) costs. Therefore, in a preferred embodiment, the distance between the puncture location (needle) and the dialysis machine is measured automatically by means of a sensor device (for example optical sensors, like laser rangefinder sensors, PMD sensors (photonic mixing device). The sensor may use triangulation for distance measurement.

In other embodiments, disposables comprise the fluids, concentrates, filters (for example dialysers and their characteristics like the ultrafiltration coefficient, clearance values and the effective membrane surface) or absorbent materials (for example their composition and/or package size).

The method is executed on a processing entity. In a preferred embodiment, the processing entity is part of the dialysis machine and may be provided as add-on module. All steps of the method are executed on the medical treatment device. In other embodiments, the processing entity may be a separate unit, for example a server, which is accessed over a network and provides the processing result as control data. The processing entity may be virtualized and also may be distributed over several processing entities.

In a preferred embodiment, the control data is provided to the medical treatment device for controlling its operation (for example time, length, and general time scheduling of medical treatment, scheduling of other resources for the treatment, kind of treatment etc.). However, a major advantage is to be seen in that the control data may be (also) provided to external machines and devices, being activatable during the course of treatment. The external machines are usually not directly mounted on the medical treatment device but do need to be equipped with an interface for data connection, in particular for receiving the control data. The external machines or devices may be peripheral devices, which may inter alia be located in the operating/treatment room, such as blinds or shutters for regulating daylight, media devices or home entertainment network, like television, and video player or radios, a heating device, which may be provided as room heating device or as treatment chair heating device.

For example, a heating device may be connected to the medical treatment system, which is adapted to emit infrared light in a certain wavelength and may be provided as infrared heater, lamp or radiator during medical treatment and which may be controlled electronically via an interface to the medical treatment system. Heat lamps can be used selectively if necessary during medical treatment to provide dry heat when other treatments are ineffective or impractical. The activation of the heat lamp during medical treatment is controlled by control data. According to a general idea, the control data is calculated automatically on the basis on several sensor signals. Thus, if a room temperature sensor measures a temperature under a preconfigured limit and/or if a body temperature sensor measures a body temperature under a preconfigure limit, a rule may be applied in order to calculate the corresponding respective control signal, for example, indicating to activate the heat lamp.

In another example, the configuration of disposables is controlled with the method. The disposables may relate to a needle system. Thus, the thickness of the needle may be controlled automatically according to the plurality of sensor data. For example, a rule data set is stored in a memory, defining rules like "if time schedule data suggests a dialysis treatment during night, then dialysis time may be increased and thus, a smaller needle diameter may be used". The control data may be provided in a text format, like text message as "use of a smaller needle diameter is possible". Of course, this is a simplified example. But it should indicate the general application. Thus, in this example, the control data comprises a needle parameter for defining the diameter of a needle, which may be for example 1.5 mm, 1.6 mm, 1.8 mm or 2 mm Some embodiments further relate to a medical treatment device for treatment of a patient, comprising:

A sensor interface for receiving sensor data from a plurality of different external peripheral sensors, A controller for processing the received sensor data in order to calculate control data and for providing the calculated control data for controlling medical treatment-related devices or for controlling the configuration of medical treatment-related apparatuses, An output interface for providing the control data.

The medical treatment device may comprise internal sensors for providing internal sensor data and wherein the internal sensor data is provided to the controller for calculating control data. The internal sensor data is processed in common and together with the external sensor data.

Some embodiments further relate to a system for medical treatment of a patient, comprising:

A medical treatment device

A sensor interface for receiving sensor data from a plurality of different external peripheral sensors, A controller for processing the received sensor data in order to calculate control data and for providing the calculated control data for controlling medical treatment-related devices or for controlling the configuration of medical treatment-related apparatuses, An output interface for providing the control data.

Certain dialysis systems described herein allow for more convenient dialysis treatments. These medical systems can, in many cases, be operated and used in a cost-effective manner. In certain embodiments, the medical treatment devices can be used for purposes beyond simply carrying out a medical treatment, such as for controlling other electronic devices. In some embodiments, an improved control of the medical treatment device can be provided based on specific selection of sensor signals.

DETAILED DESCRIPTION

Figure 1:
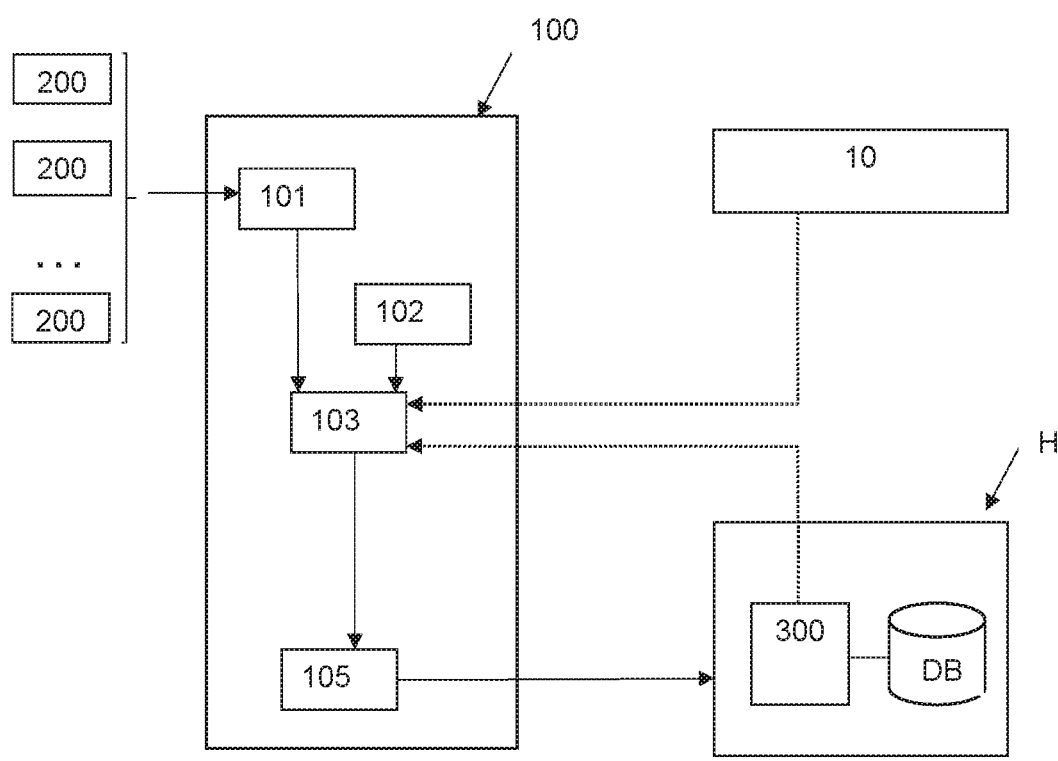
FIG. 1 shows a schematic overview of a medical apparatus in the preferred embodiment of a dialysis machine.

The medical treatment device is a machine for providing healthcare services. According to a preferred embodiment, it refers to a dialysis machine, particularly a home dialysis apparatus for home use, which may be embodied as a hemodialysis machine or a peritoneal dialysis machine. In other embodiments, the medical treatment device may relate to a hemofiltration, or to a hemodiafiltration machine.

The medical treatment related device may be any kind of electronic device or machine, which may be used during medical treatment and comprises an interface for receiving control signals, in particular during the course of treatment. In a preferred embodiment, it may refer to a video player, to a music player, to a media presentation device, to a lighting system and/or to a heating device. In another preferred embodiment, the medical treatment related device relates to a control device of a home network, which through the network controls further devices which are connected to the home network. Hence every device, which is controlled using the home network, can also be controlled. The medical treatment related device may be an internal assembly element of the medical treatment device (i.e. a display, loudspeaker) or may be an external device as mentioned above. The sensor data is received on a plurality of (different types of) sensors, which may be located at different positions. It is also possible to use sensors on wearables, like a smart watch, a smart wristband or a smartphone for detecting patient-related sensor data. The sensor data comprises digital and analog signals, like location data, body and/or room temperature etc. The sensors may be adapted to receive medical and healthcare-related data, like physiological data (pulse, blood pressure etc.). The sensors may also be designed to receive non-healthcare data, like position data (as position sensors), light data, temperature data, humidity data, blind or shutter control data, volume data for acoustic emissions etc.

Embodiments are described in the following with particular reference to the controlling of a dialysis machine 100. It is emphasized that the implementation is not restricted to the illustrated embodiments but is rather possible in connection with other medical treatment devices.

Home dialysis is becoming an increasingly popular alternative to in-center dialysis. In order to dialyze in the comfort of one's own home, the patients must keep to a schedule, set up their own machine, keep track of supplies, monitor their own treatment, and disinfect their own machine afterwards. With other words, the patient has a burden to execute a plurality of steps in a reliable manner so that his treatment safety is maintained. This in turn requires that the patient is highly motivated.

Improving patient outcomes may be an advantage of creating a more intelligent dialysis machine that uses a plurality of sensor data. The dialysis machine 100 is equipped with an intelligent control module, which may be software or hardware based (and may for example be provided as FPGA, field programmable gate array). With the new control the dialysis machine 100 may, for example, fill the role of a personal trainer.

Motivating a home dialysis patient is especially challenging because the patient is outside of the clinical environment where the clinic staff may intervene. Most of the work must be done by the patient and/or the patient's caregiver. When a patient skips a critical treatment due to lack of motivation, accumulating toxins are not removed from the patient's bloodstream and, over time, this usually leads to serious health consequences.

FIG. 1 schematically illustrates a preferred embodiment of an inventive medical treatment device in the form of a dialysis machine 100 for home use.

The dialysis machine 100 is configured with an electronic module. The electronic module may comprise a sensor input interface 101 for receiving data, in particular, sensor data from a plurality of sensors 102, 200. The sensors may be mounted on different peripheral devices, comprising external electronic devices (external sensors 200) and internal devices (internal sensors 102). Internal devices are related to the dialysis machine 100. They may be mounted in the machine (e.g. door opening sensors) or may be attached to peripheral devices (e.g. on supply tools). The electronic module further comprises a controller 103 for processing received sensor data and for providing control data. An output interface 105 is provided on the electronic module as well. It serves for providing a result of the processing, inter alia for providing control data. The control data serves to control the medical treatment process, more specifically the dialyses and related steps.

The electronic module for executing the method may be implemented in software and may be downloaded form a server 10 as depicted in FIG. 1 as an option with the dotted line in order to represent that the computer program may be downloaded into a memory of a processing unit. The software may also directly be provided on an (embedded) microcontroller. The computer program may also be embodied as electronic circuit and/or as software an electronic processing unit of the medical treatment device 100.

As can be seen in FIG. 1, sensor data is aggregated from a plurality of different sensors 102, 200 in pre-configurable time intervals on the input interface 101. The received sensor data (digital data and analog signals) is then transferred to the controller 103 for automatic processing. The controller 103 provides control data and may forward the same to a central server 300, which may be located in a hospital's H information technical system. The server 300 may access a database DB. The database DB may serve as storage for storing sensor and/or control data. It may further serve as a rule database for providing a set of processing rules. Alternatively, the rules database may be swapped out on a separate database. This has the advantage that the rules may be amended independent of the operation of the system. The rules may also be adapted dynamically, based on the received and processed sensor data.

The sensor data may be captured on different medical devices as pulse of the patient, blood pressure, respiratory rate, skin conductivity, body temperature etc. The measured data may be cached and may be averaged over a certain time interval. The sensors may also be adapted to receive non-medical or non-physiological data. For example, the sensors may be provided as room temperature sensors, location sensors, step counters, sensors in wearable devices etc.

Some embodiments make intelligent use of the "smart" technology found in wearable devices such as smart-watches and smart-phones (smart wristbands, smart shoes, smart rings etc.) in a dialysis machine 100 to learn about the patient's behavior, to monitor a patient, and keep track of a patient's schedule to more seamlessly integrate dialysis treatments and machine maintenance into the patient's existing routines. Dialysis machine's 100 hardware may include GPS, Bluetooth, Wifi, NFC, microphones, infrared sensors and/or other communication equipment to facilitate interaction with a patient's own "wearable technology". The term "wearable technology" refers to smart electronic devices (electronic device e.g. equipped with microcontrollers or microprocessors) that can be worn on the body, as implant or accessories. It is possible to incorporate practical functions and features in the devices (like step counter, scheduling devices, weight measurement etc.). For example, the electronic wearable devices with their sensors may be provided as optical head-mounted displays as smartwatches, smart wirstbands and/or as activity trackers. The sensors of the electronic wearable devices may comprise for example photoplethysmography sensors, which may illuminate the patient's skin and measure changes in light absorption in order to determine Blood Volume Pulse (BVP), from which heart rate, heart rate variability (HRV), and other cardiovascular features may be derived. Other sensors may comprise for instance (3-axis-) accelerometer for capturing motion-based activity, electrodermal activity sensors for measuring electric parameters of the patient's skin (like resistance, potential, impedance, admittance), which may be used to detect sympathetic nervous system arousal and to derive features related to stress, engagement, and excitement, or sensors for measuring the peripheral skin temperature, like infrared thermopiles. The external sensors 200 can also collect biometric data such as heart rate (ECG and HRV), brainwave (EEG), and muscle bio-signals (EMG) from human body to provide valuable information in the field of health care and wellness. This data will be aggregated and processed in order to provide control data.

The control data serves for controlling electronic means and devices which may be activated during the course of treatment and may even control the medical treatment and elements of the medical treatment device itself (components thereof). The means and devices to be controlled may thus be positioned inside or attached to the medical treatment device or may be positioned as external elements (like heating system, lighting system, multimedia devices). The external means and devices may be connected via radio connection or via WLAN or LAN or Bluetooth to the output interface 105 of the machine 100.

Also, other sensors may be connected. The sensors may be external sensor 200, as mentioned above and also internal sensors 102, which may be part of the dialysis system or even may be directly mounted on the dialysis machine 100. The dialysis machine software would be written to harvest and intelligently compile data from these peripheral sensors 200, 102 in order to learn about the patient over time. With this newly gathered data it may be possible to automatically generate healthcare related suggestions or machine related suggestions (for example for maintenance services of the machine or for replenishment of disposables or other resources). The technical effect may also be achieved to keep track of machine execution and parts thereof. Moreover, it is possible to make technical operation of the dialysis machine much easier, for example, by automating functions through voice command. The dialysis machine 100 becomes more than a static piece of equipment and instead both actively and subtly encourage the patient to undergo efficient and less effort intensive life-sustaining treatments to gently improve health outcomes.

Figure 2:
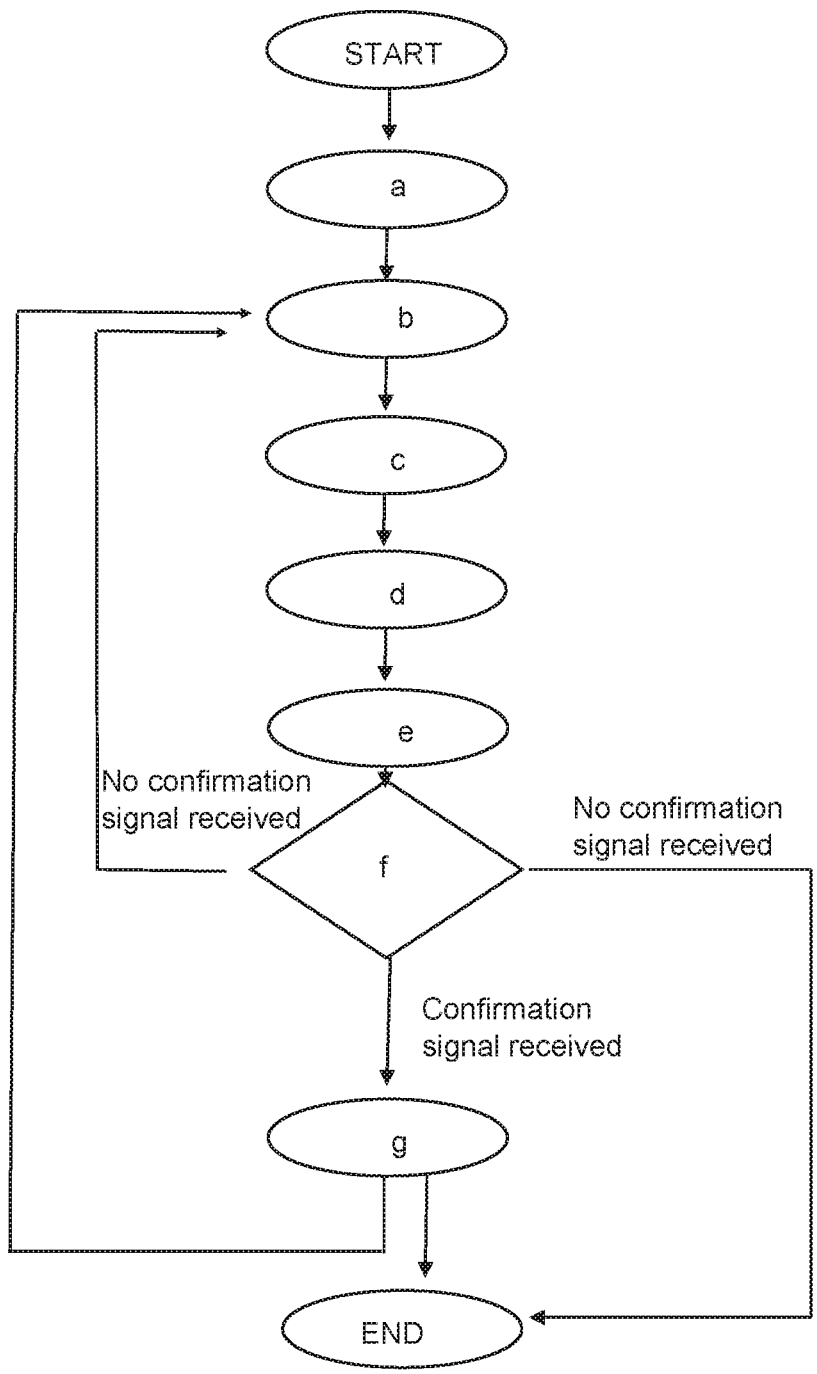
FIG. 2 is a flow chart of a control method according to a preferred embodiment.

FIG. 2 shows a workflow of a control method according to a preferred embodiment. After start of the method, in step a, an activation signal is received. The activation signal may be inputted on a user interface by a user for initiating the automatic treatment control. Step a, however, is not mandatory. It is also configurable to initiate the automatic control independent of a user activation signal.

In step b, sensor data is received from the plurality of different sensors 102, 200.

In step c, the received sensor data is processed in order to provide control data in step d.

The automatically calculated control data may be provided on a user interface for information of the patient in step e. This step e, however, is optional. In step f, a confirmation signal is received. The confirmation signal serves to validate the automatic control of the treatment process by the control data. If the patient does not agree to such a control, he/she may refrain from inputting the confirmation signal in order to prevent automatic control with said control data. Then, control data may be changed or may be adapted manually.

In step g, a status report may be forwarded to the central server 300 or to other computer based instances for example for central storage. After this, the method may end or may be repeated iteratively, beginning again for example at step b. As shown in FIG. 2, after step d the method may also end or may branch out to step b.

In general, steps e, f and g are optional.

In a preferred embodiment, the step of receiving sensor data may be executed over a time period and even during the time when the data is processed in step c. Thus, steps b and c may be executed in parallel. This has the advantage, that the control data may be based on the most actual and latest sensor data. The controller 103 may be adapted to actively request sensor data from an internal storage in order to process the same.

Figure 3:
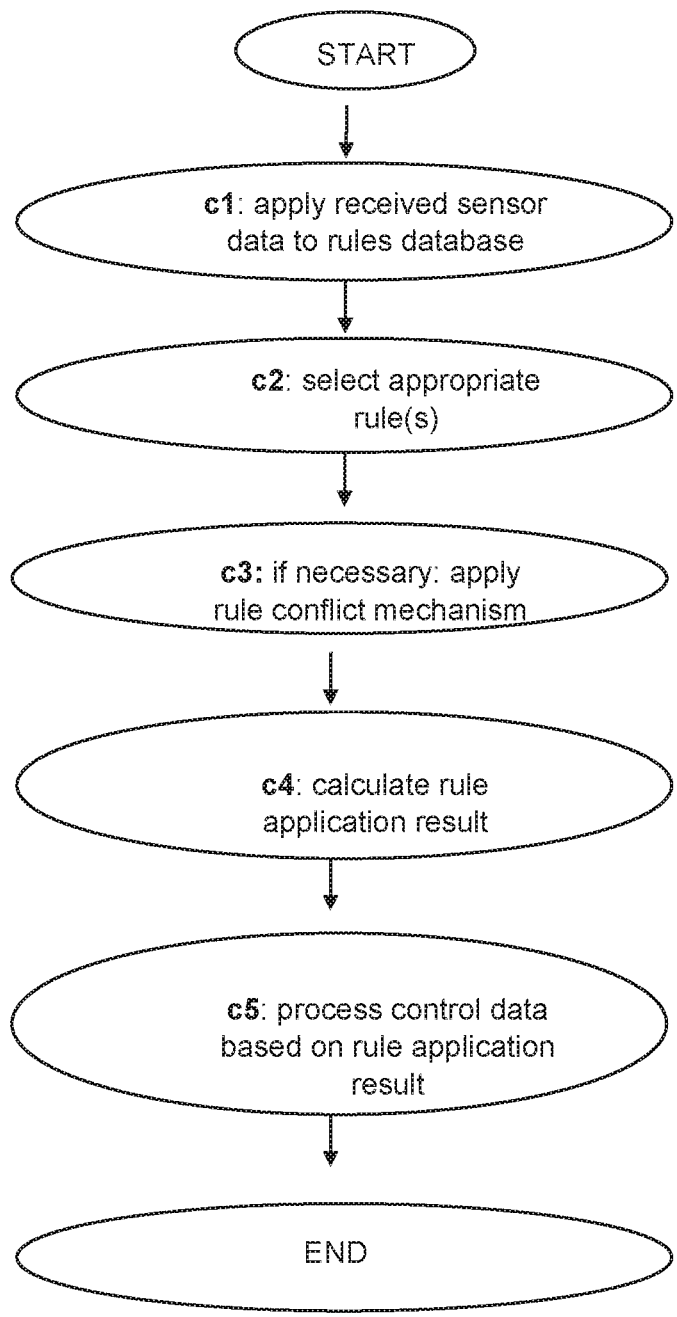
FIG. 3 is a flow chart of a processing step of the control method, depicted in FIG. 2 according to a preferred embodiment.

The processing step c will be described in more detail with respect to FIG. 3. The processing of the received sensor data is executed fully automatically and in a preferred embodiment without any further user interaction. The processing may be executed on the controller 103, directly on the dialysis machine 100. In other embodiments, this processing step may also be swapped completely or partially to external electronic modules, to a processor, to another computing instance or may even be virtualized. The processing may also be centralized and executed on the central server 300. In step c1 the received sensor data is prepared and transferred to the respective computing instance for an application of pre-configurable rules. In step c2 a set of rules are selected which are appropriate for the specific received sensor data. For example, if only temperature data is received from a body temperature sensor and from a room temperature sensor, these temperatures signals may be pre-processed (e.g. averaged) and the set of rules has to be selected, which deals with temperature data like e.g. "IF 'temperature value' is below a pre-configured threshold, THEN define a heating initiating signal as control data", which when being executed will activate the heating device accordingly. This example, is of course simplified. In reality, conflicts may arise. For example, if physiological patient data (and the application of a respective rule) suggest to increase temperature, whereas other sensor data, for example energy or cost related data suggest not to increase the temperature, a conflict arises, which will be resolved. In case of such a conflict, a rule conflict mechanism is applied in step c3. The rule conflict mechanism resolves the conflicts. In a very simple embodiment, this is done by prioritizing rules. The prioritizing may be represented in a table in a certain memory. In step c4 a rule application result is calculated. In step c5 the control data based on the rule application result will be processed. After step c5 the method may end.

Figure 4:
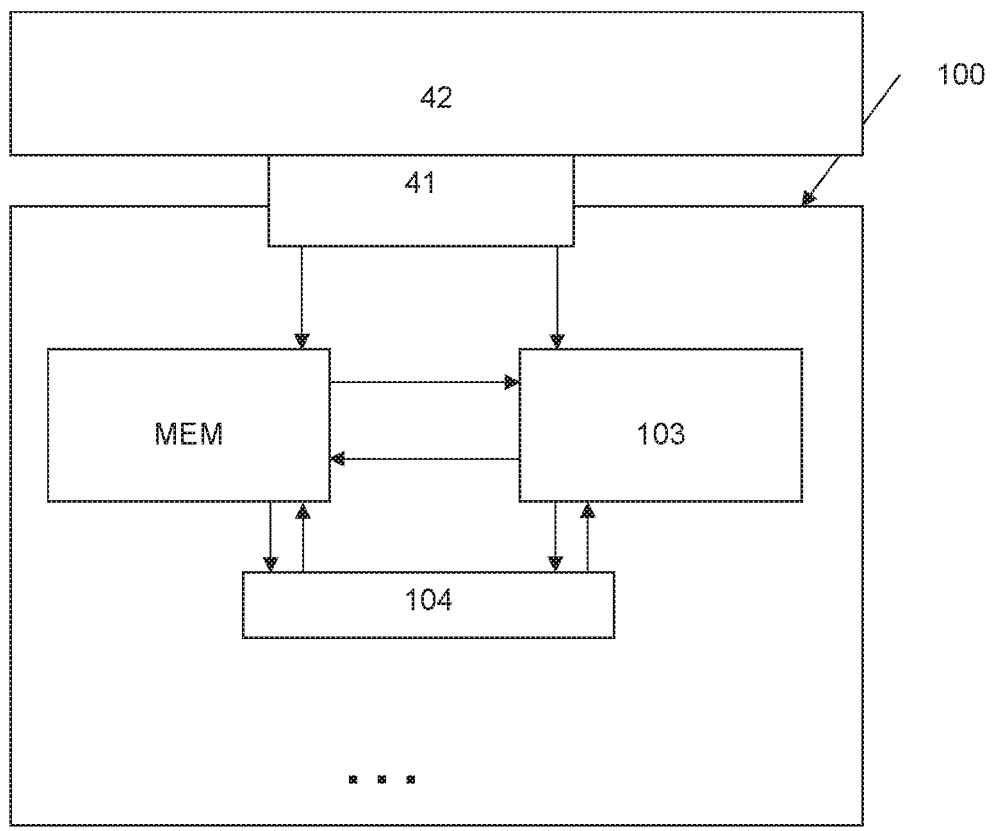
FIG. 4 is a schematic representation of possible electronic units for implementing the control method, according to a preferred embodiment.

FIG. 4 shows the electronic module of a dialysis machine 100 in a schematic exemplary representation. The dialysis machine 100 comprises a protocol interface 41, which serves to receive input data via a particular protocol. According to a preferred embodiment, the protocol is based on and may be connected to a CAN bus system 42. In other embodiments also other bus systems may be used, like Ethernet or a RS232 bus system. The input data may relate to a computer program for implementing the method, described above. The input data may also relate to non-functional data. The computer program may be loaded in a memory, for example in the main memory. The controller 103 is adapted to access the main memory for execution of the computer program. The memory may preferably be a Flash EEPROM. The controller 103 may also be realized by a microcontroller or by a microprocessor 104 or may in part be realized in an operating system of the dialysis machine 100. As represented in FIG. 4 with the three dots, it is of cause possible to provide additional modules for providing additional functions, like a memory for additional storage capacity, a cache memory for caching received sensor data and the like.

In the following description three preferred embodiments are described.

In a first embodiment, the home dialysis patient is wearing a smart-watch at home, having fallen asleep in a recliner. The Smart Home Dialysis machine 100 has learned the patient's prescription and schedule and notes that the patient is at home and asleep based on the heartrate detected by the smart-watch. The machine 100 automatically checks the patient's social calendar and notes that patient's evening is free and the patient's favorite TV show is beginning. The machine 100 sends a YES/NO confirmation check to get ready for treatment to the patient's smart-watch, waking up the patient. The patient confirms that she/he is ready for an earlier treatment time. The machine 100 automatically fully powers on and begins running self-tests followed by automated treatment setup. The machine 100 sends a control command (within the control data) to home entertainment network to begin recording patient's TV show and sends an activation control signal in order to turn on the TV in front of the machine 100 so the TV show can be played when patient is seated for treatment. Patient enters the room, makes simple connections by himself or herself and sits for treatment as the machine 100 runs and the TV show is played. After treatment, the machine 100 notes usage of dialysis supplies and sends a message to dialysis clinic to send new supplies in next shipment.

In a second embodiment, a home dialysis patient is riding in car towards home with smartphone docked in the car's console. The machine 100 notes that patient was just dialyzed yesterday but also checks the patient's social calendar and notes that the patient was attending a baseball game in which the patient's favorite team has won and assumes that the patient drank an extra amount of fluid during the baseball game. The machine 100 sends a YES/NO confirmation check to get ready for an extra treatment to the patient's smart-phone. The patient confirms he/she is ready for an extra treatment. The patient may send back using the smart phone the information of the volume of the extra amount of fluid. The machine 100 adjusts prescription to nephrologist-approved treatment profile to ultrafilter the extra fluid from patient and the machine 100 begins automated setup to be ready when patient arrives home for treatment. The machine 100 connects to the patient home's smart-thermostat and increases the room temperature to match the patient's comfort level. The machine 100 connects to the patient home's lighting system and illuminates the hallway leading to the treatment room. The machine 100 connects to the patient's home assistant, e.g. Amazon Echo, and plays patient's favorite music. During treatment, the machine 100 sends treatment data in real time to nephrologist to demonstrate efficacy of new prescription settings.

Generally, it is possible that the machine 100 requests a separate confirmation signal for each of the different control suggestions (in the example above for the thermostat, lighting system, home assistant, treatment data sender). In another embodiment, only one confirmation signal is requested for the set of intended controls (transferred by means of control instructions to the particular electronic nodes). The electronic nodes (means and/or devices to be controlled by means of the control data, prepared by the medical treatment device 100 (which is synonym for the machine)) are connected to the machine 100 via cable or wirelessly in order to receive the control data from the output interface 105. In particular, this may be an IP-based protocol connection.

In a third embodiment, the home dialysis patient uses an iPad with an application/app installed to book a three-day trip away from home. The machine 100 notes change to patient's schedule and proposes an extended treatment prior to the trip with a suggested dialysis start time in order to be finished with the dialysis treatment in time to arrive at airport by scheduled departure based on traffic conditions. The machine 100 then emails to the patient a list of kidney-friendly restaurants and menu selections in the destination city. On the second day the patient is away, the machine 100 automatically powers on and performs a heat disinfection and then powers down. On the fourth day since the trip began, the machine 100 notes that patient has not yet returned home and connects with patient's smart-wristband, confirming patient is still in destination city. The machine 100 contacts patient's caregiver with a list of dialysis clinics nearby the patient with recommendations for treatment. Patient's caregiver selects a dialysis clinic and takes patient for treatment while the machine 100 uploads the patient's prescription and medical information to clinic's dialysis network for seamless treatment transfer.

Certain aspects may provide several advantages. For the unmotivated patient, the home dialysis machine can be as unappealing as home gym equipment. By creating a Smart Home Dialysis machine 100 equipped with the extra smart control functionality, the machine can become the patient's "personal trainer" and remove many common obstacles to home dialysis treatments. Never before has a dialysis machine been so integrated into a patient's life, being able to deliver smart reminders, make diet suggestions, automate treatment setup and machine maintenance, keep track of supply inventory, and mesh with existing smart-technology to yield the best possible health outcomes in the most comfortable ways.

In another preferred embodiment, position data may be used as sensor data, which indicates that the patient is travelling by car (or otherwise) and which will initiate further reception of traffic news in order to evaluate whether the patient might be late due to traffic jams or if he or she will arrive in time. Additionally, temperature may be detected and processed as sensor signal, too. The temperature sensor signal may be processed and used in order to adapt the room temperature, when the patient will enter the room for dialysis treatment. At least in part, the machine 100 may also provide control data for controlling the temperature of the dialysate, when being applied to the patient. This may serve that the patient fills more comfortable, when for example sensor signals suggest that he/she feels cold, dialysate temperature may be increased.

According to another preferred embodiment, the sensor data may be received via a query which is directed to the patient and which may be provided on a display for representing questions, such as "Do you feel cold/warm?", "Are you hungry?", "Do you want to listen to music?". The user may use his mobile device or another option for providing his answers to the questions. These answers may also be detected as sensor signals and may be processed according to rules in order to provide control data. The control data in the examples before may then relate to control of seat/room temperature, requesting the service of a meal delivery service and for controlling the music player. Further questions and respective controls may relate to a control for providing emails, for providing stock exchange or sport results, for selecting a TV or radio channel etc. The questions may be pre-configured and may be selected from a list for initiating control of the respective assigned devices.

In another embodiment, the physiological data of the patient is processed, indicating for example a relative high fat degree in tissue. Then, based on this intermediate result, a further control signal could be generated in order to only suggest appropriate meals (i.e. diet meals, low fat meals etc.). Also, further information may be provided on a user interface for informing about ingredients which may influence the medical treatment, for example by informing about the intradialytic fluid absorption.

If for example the detected physiological data or data provided in the form of answers (by the patient himself or herself) indicates, that the patient wants to fall asleep, then control data may be provided in order to support this goal, by reducing volume of speakers, by reducing daylight by automatic control instructions for closing the shutters by deactivating telephone etc. The respective control signals are generated autonomously and will be forwarded to the respective device for the purpose of controlling the same in the period of treatment. However, special use cases may suggest that an initiation of a sleep state may not be helpful, because, for example, other sensor data suggests, that the patient has a meeting directly after the treatment. In this case, the calendar entry based sensor signal and the sleep target state are processed by accessing the rules database in order to learn that a sleep state will not be actively initiated in case a subsequent meeting is scheduled.

In a preferred embodiment, additional sensors are used in the form of applications which are directed to automatically detected a person's sleep phase, like REM, Non-REM phases, for example based on respiratory sounds or other signals. Then, the patient may be waked up only in a light sleep phase or REM phase, which will lead to a very smooth and gentle waking.

During sleep state, usually pulse and blood pressure will decline. By detecting these sensor signals, control data may be provided for adapting the flow of blood during dialysis treatment, namely to reduce the same for not straining the body circulation. This in turn, will increase the time period used for dialysis treatment and the therapy goal may in turn be adapted accordingly. Preferably, a confirmation signal is requested by the user. The therapy goal may be defined by a dialysis dose as value indicating a relation of an urea clearance over time, defined as Kt/V, wherein K refers to urea clearance, t refers to time and V refers to the urea distribution volume. During sleep state, the ultrafiltration rate may be reduced in accordance with the longer dialysis time (during the night) in order to reach the therapy goal. An additional volume of substitution solution for a hemodiafiltration procedure can be administered and will influence the whole ultrafiltration result and may be amended respectively. In this respect, generally, a reduced ultrafiltration rate is preferred, since this involves a gentler treatment for the patient.

In another preferred embodiment, the blood pump may be controlled by the control signal. The control signal may be based on the patient's pulse, which is detected as sensor signal. Thus, the blood pump may be controlled in accordance with the pulse for not adding additional pressure to the vascular system of the patient. Preferably, impeller pumps and centrifugal pumps are used and controlled, which do not generate an additional pressure pulse in contrast to hose reel pumps and which are easy to control. In this embodiment, the pump may be controlled synchronously to the natural patient pulse and representing the same respectively. The patient's pulse may be detected by means of a pulse sensor and/or may be detected in the extracorporeal blood circulation system when using impeller pumps (for example by means of a pressure sensor).

In another embodiment, it is possible to control the medium blood flow in dependence (and accordance) of (to) the detected pulse. For this purpose, the processing device 103, 104 may access a rule database. There, a rule may be stored, which indicates that medium blood flow should be increased for a higher pulse and should be decreased for a lower pulse. This is particularly possible, when using an impeller pump. In general, a pulse synchronous control of the blood flow is possible.

In another embodiment, exemption rules may be stored in the rule database, indicating and representing situations in which a non-compliance with the pre-set therapy goal may be tolerated exceptionally. This situation may for example relate to specific detected physiological values and/or to a certain time period. The control of the dialysis process (or treatment) may be based on certain decisions, taken autonomously by the system by accessing the rules in the rule database. These autonomous decisions (for example to increase dialysis time) may be subject to a confirmation signal on a user interface. This confirmation signal may be output to the patient directly or to a central administration unit at a hospital or a caregiver. Other rules may relate to actually detected parameter values. For example, if the system detects a sudden significant increase in the pulse, an alert message may be generated and provided as output. Moreover, balancing control signals may be generated. It is also possible to generate a question to the patient for asking about the circumstances and reasons for the detection of the sudden increase. In case the patient provides a reasonable answer, the alert message may be deleted again.

In a preferred embodiment, all data that is detected and processed are stored and are fed back to the system again for further control. In particular, all detected sensor signals or sensor data and all calculated control data are stored in an interrelated manner. It is detectable which kind of sensor data is mapped to which kind of control data and whether the control data has been confirmed by the confirmation signal. Thus, it is possible to refer to past treatments (with historical data) for generating the control data for present or future treatments. For example, if past sensor data indicates, that usually the patient activates dialyses during night time, this information may be processed by means of at least one rule in the rules database to indicate a smaller needle diameter to be used due to a longer dialysis time. This suggestion may be provided automatically to the patient as suggestion, which may be confirmed or rejected on a user interface. Again, this feedback user input will be stored and may be used for future processing. In the example, mentioned above, an extended dialyses treatment time will be applied.

This information may also be used by the system and processed in order to provide a control signal for scheduling subsequent appointments, for example postponing a meeting, which is scheduled after the treatment in case of a longer treatment time.

Further, it is possible to monitor a sequence or set of several dialysis treatments and to detect an average value for a number of treatments. Then, it may be tolerated that the therapy goal is not achieved in one single treatment, provided that the other treatments in the same sequence are adapted accordingly so that the therapy goal may be achieved for the whole treatment sequence over a configurable set of treatments.

The features in the above description, the drawings and the claims can be of significance individually or in combination or in sub-combination for the realization of various embodiments.

LIST OF REFERENCE NUMERALS 100 medical treatment device, in particular dialysis machine for home use
101 input interface
102 internal sensor(s)
103 controller
104 microprocessor
105 output interface
300 server
DB database
H medical facility, hospital
10 service instance
41 protocol interface
42 bus system, in particular CAN bus
a activation of automatic control
b receive sensor data
c process received sensor data
d provide control data
e provide control data on user interface
f receive confirmation signal
g forward status report to central server 300
c1 apply received sensor data to rule database
c2 select appropriate rule set
c3 apply rule conflict mechanism
c4 calculate rule application result
c5 process control data based on rule application result

The invention claimed is:

1. A medical treatment device for treatment of a patient, comprising:
a sensor interface configured to receive sensor data from a plurality of different external peripheral sensors;
a controller configured to:
process the received sensor data to calculate control data;
receive a confirmation signal indicating user validation of the control data; and
provide the control data for: (i) controlling at least one medical treatment-related device, the at least one medical treatment-related device being a dialysis machine and/or related medical devices and (ii) controlling, during a medical treatment, a setting of at least one non-medical external device to adjust the patient's ambient conditions of at least one of light, sound, or temperature, the at least one non-medical external device selected from the group consisting of radio, media device, telephone, headphones, heating devices, electronically controllable blind or shutter, a lighting system, and/or a control device of a home network configured to control one or more devices connected to the home network; and
an output interface for providing the control data;
wherein, if the confirmation signal indicating user validation of the control data is not received, the controller is configured to prevent automatic control of the at least one medical treatment-related device and the setting of the at least one non-medical external device based on the control data.

2. The medical treatment device according to claim 1, further comprising internal sensors configured to output internal sensor data to the controller, and wherein the controller is configured to process the internal sensor data to calculate the control data.

3. The medical treatment device according to claim 1, wherein the sensor interface is a wireless interface.

4. The medical treatment device according to claim 1, wherein the output interface is a wireless interface.

5. The medical treatment device according to claim 1, wherein the medical treatment device includes a blood pump and the control data is used to control a flow rate of the blood pump.

6. The medical treatment device according to claim 1, wherein the medical treatment device comprises a peritoneal dialysis machine.

7. The medical treatment device according to claim 1, wherein the sensor data comprises data selected from the group consisting of: location data, physiological data, temperature data, and scheduling data detectable in an electronic calendar.

8. The medical treatment device according to claim 1, wherein the sensor interface is configured to receive sensor data from one or more wearable devices.

9. The medical treatment device according to claim 1, wherein the sensor data comprises one or more of:
location data indicative of a position of the patient;
movement pattern data defining typical movements of the patient in connection with medical treatment;
environmental data indicative of physical values for the medical treatment device; and
medical status data of the patient.

10. A system for medical treatment of a patient, comprising:
a medical treatment device;
a sensor interface configured to receive sensor data from a plurality of different external peripheral sensors;
a controller for processing the received sensor data in order to calculate control data, for receiving a confirmation signal indicating user validation of the control data, and for providing the calculated control data for: (i) controlling at least one medical treatment-related device, the at least one medical treatment-related device being a dialysis machine and/or related medical devices and for (ii) controlling, during a medical treatment, a setting of at least one non-medical external device to adjust the patient's ambient conditions of at least one of light, sound, or temperature, the at least one non-medical external device selected from the group consisting of radio, media device, telephone, headphones, heating devices, electronically controllable blind or shutter, a lighting system, and/or a control device of a home network configured to control one or more devices connected to the home network; and
an output interface for providing the control data;
wherein, if the confirmation signal indicating user validation of the control data is not received, the controller is configured to prevent automatic control of the at least one medical treatment-related device and the setting of the at least one non-medical external device based on the control data.

11. The system according to claim 10, wherein the sensor interface is a wireless interface.

12. The system according to claim 10, wherein the output interface is a wireless interface.

13. The system according to claim 10, wherein the at least one medical treatment-related device is a mobile device or a stationary device.

14. The system according to claim 10, wherein the medical treatment device includes a blood pump and the control data is used to control a flow rate of the blood pump.

15. The system according to claim 10, wherein the medical treatment device comprises a peritoneal dialysis machine.

16. The system according to claim 10, wherein the sensor data comprises data selected from the group consisting of: location data, physiological data, temperature data, and scheduling data detectable in an electronic calendar.

17. The system according to claim 10, wherein the sensor interface is configured to receive sensor data from one or more wearable devices.

18. The system according to claim 10, wherein the sensor data comprises one or more of:
location data indicative of a position of the patient;
movement pattern data defining typical movements of the patient in connection with medical treatment;
environmental data indicative of physical values for the medical treatment device; and
medical status data of the patient.

19. The system according to claim 10, wherein the sensor data comprises physiological parameters, and wherein the control data comprises a blood pump control signal for controlling a blood pump.

20. The system according to claim 10, wherein threshold values are configured for all the sensor data, and wherein the controller is configured to output an alert signal in response to non-compliance with the threshold values.

* * * * *

UNITED STATES PATENT AND TRADEMARK OFFICE
CERTIFICATE OF CORRECTION

| | |
|---|---|
| PATENT NO. | : 12,048,790 B2 |
| APPLICATION NO. | : 17/074184 |
| DATED | : July 30, 2024 |
| INVENTOR(S) | : Alexander Heide, Karsten Fischer and Stephen A. Merchant |

It is certified that error appears in the above-identified patent and that said Letters Patent is hereby corrected as shown below:

On the Title Page

Item (73) Assignees:, Line 2, delete "Medical" and insert --Fresenius Medical--.

Signed and Sealed this
Twelfth Day of November, 2024

Katherine Kelly Vidal
*Director of the United States Patent and Trademark Office*